United States Patent [19]
Murray, Jr. et al.

[11] Patent Number: 4,801,655
[45] Date of Patent: Jan. 31, 1989

[54] FIBER OPTIC PH SENSOR HAVING LOW DRIFT RATE

[75] Inventors: Richard C. Murray, Jr., Palatine, Ill.; Mark S. Goorsky, Somerville, Mass.

[73] Assignee: Gould, Inc., Ill.

[21] Appl. No.: 88,535

[22] Filed: Aug. 20, 1987

Related U.S. Application Data

[63] Continuation of Ser. No. 747,488, Jun. 21, 1985, abandoned.

[51] Int. Cl.[4] ................................................. C08F 8/12
[52] U.S. Cl. .................................. 525/329.4; 525/369; 8/555
[58] Field of Search ...................... 525/369, 329.4; 8/4

[56] References Cited

U.S. PATENT DOCUMENTS

| | | | |
|---|---|---|---|
| 3,984,204 | 10/1976 | Jenkins et al. | 23/232 F |
| 4,166,804 | 9/1979 | Bleha et al. | 252/408 |
| 4,194,877 | 3/1980 | Peterson | 8/647 |
| 4,200,110 | 4/1980 | Peterson et al. | 128/634 |
| 4,378,971 | 4/1983 | Schwartz | 436/66 |
| 4,466,941 | 8/1984 | Cerami | 422/57 |
| 4,476,870 | 10/1984 | Peterson et al. | 128/64 |

Primary Examiner—Joseph L. Schofer
Assistant Examiner—B. Lipman
Attorney, Agent, or Firm—Lyon & Lyon

[57] ABSTRACT

A hydrolyzed dye/gel polymer for use in a pH-based sensor is characterized by its chemical and optical stability with respect to dye loss with time. Preferably, the dye/gel polymer is hydrolyzed by heating in a dilute base solution for a period of time sufficient to remove weakly bonded dye molecules from the polymer, then washed to remove the base solution and loose dye.

10 Claims, 2 Drawing Sheets

STABILITY COMPARISON

FIBER OPTIC PH SENSOR HAVING LOW DRIFT RATE

This application is a continuation of application Ser. No. 747,488, filed June 21, 1985, now abandoned.

BACKGROUND OF THE INVENTION

This invention relates generally to fiber optic chemical sensors and more particularly to the pH-sensing hydrogel (dye/gel polymer) used in such sensors.

pH-sensors are based on the principle that certain materials' optical properties change with pH. For example, D. Lubbers et al., "Nanoencapsulated Fluorescence Indicator Molecules Measuring pH and $pO_2$ Down to Submicroscopical Regions on the Basis of the Optode-Principle", Z. Naturforsch., 32c, 133–134, 1977, used a fluorescent material ($\beta$-methyl umbelliferone) encapsulated in polymer beads having porous outer membranes to measure pH. The fluorescent intensity of the material is proportional to pH. Peterson et al., "Fiber Optic Probe for Physiological Use", Anal. Chem., 52, 864–869, 1980, used a colorimetric pH-indicating dye (eg. phenol red) bound to polyacrylamide hydrogel by copolymerization of the dye with the acrylamide monomer in the preparation of their fiber optic pH-sensing probes. The dye changes color with changes in pH, and the color change corresponds to a change in the amount of light of a specified wavelength absorbed by the dye (eg. green light in the case of phenol red). The Peterson et al. fiber optic probe (also described in U.S. Pat. No. 4,200,110) as shown in FIG. 1 consists of an ion permeable membrane 11 which encloses the distal ends of a pair of optical fibers 12, 13. Retained within the hollow membrane 11 and distal to the distal ends of the optical fibers is the pH-indicating sensor (dye/gel polymer) 14. Fiber 12 provides light to sensor 14 and fiber 13 transmits the absorbable light from sensor 14. Thus, the pH of a solution placed in contact with a column of sensing gel, through the ion permeable membrane, can be determined by the intensity of the absorbable light transmitted through the optical fibers.

pH sensors and pH-based sensors which are used for applications such as continuous patient monitoring are typically manufactured, calibrated, and then sold for use. Once used, the sensors are thrown out. pH sensitive dye/gels change color or fluorescence as a result of changes in the pH of the solution. For analytical purposes it is critical that the color or fluorescent intensity of the dye/gel be constant for a given pH. Sensors made with the conventional dye/gel polymer show a substantial drift in measured pH with time, resulting from a continual decay in the absorbence of the dye/gel. This drift also corresponds to an increase in the protonation constant, K, of the gel, and severely limits the accuracy of the sensors for pH measurements over extended periods of time (i.e., more than a few hours), or necessitates frequent recalibration of the probes. Furthermore, the initial optimum operating range of these sensors is variable and also drifts with time because of changes in K. All of these factors contribute to a serious lack of reliability in pH-sensors which impedes their use for continuous patient monitoring.

Therefore, it is an object of the present invention to provide a dye/gel polymer suitable for use as a pH-sensor having minimal drift.

It is another object of the present invention to provide a dye/gel polymer, having a consistently repeatable K value, suitable for use as a pH-sensor.

It is yet another object of the present invention to provide a chemically stable pH-sensing probe, having minimal drift, suitable to be implanted in tissue for physiological studies.

It is also an object of the present invention to provide an optically stable pH-sensing probe, i.e. one in which the color or fluorescence is stable for a given pH.

Additional objects, advantages, and novel features of the invention will be set forth in part in the description which follows, and in part will become apparent to those skilled in the art upon examination of the following or may be learned by practice of the invention.

SUMMARY OF THE INVENTION

The invention consists of a special treatment of the dye/gel polymer which changes its structure sufficiently to render it chemically and optically stable. While not wishing to restrict themselves to any particular theory as to why their treatment solves the aforementioned problems, the inventors believed the cause of the sensor drift was due to the gradual loss of weakly bonded dye molecules from the polymer structure. The inventors determined that when the initially prepared dye/gel polymer is partially hydrolyzed, the polymer's structure is changed such that substantially all loosely bound dye molecules are removed. The hydrolyzed dye/gel polymer is characterized by chemical and optical stability with respect to dye loss with time. Untreated sensors, when stored in solution release dye and thereby lose calibration. Treated sensors, when stored in solution, release an insignificant amount of dye and retain their calibration with respect to time. Furthermore, the treated dye/gel polymer's effective dissociation constant becomes more consistent from batch to batch and resulting sensors are optically stable with respect to color or fluorescence for a given pH.

A hydrolyzed dye/gel polymer characterized by chemical and optical stability with respect to dye loss with time is preferably prepared by the following technique. The dye/gel polymer is first treated in a dilute base solution for a period of time sufficient to remove the weakly bonded dye molecules from the polymer. The time period depends generally on the temperature at which the process is carried out. Then the dye/gel polymer is washed to remove the base solution and resultant loose dye.

DESCRIPTION OF THE DRAWINGS

A typical fiber optic probe is shown in FIG. 1.

Plots of pH versus time for untreated sensors and treated sensors are shown in FIG. 2. The treated sensor has substantially constant response whereas the untreated sensor's response decreases significantly with time and is not reproducible.

DETAILED DESCRIPTION OF THE INVENTION

While many variations in the following treatment will become apparent to those skilled in the art, this particular example produced significant and reproducible results. One gram of synthesized dye/gel polymer (containing phenol red) is added to 100 ml of aqueous 0.025M NaOH in a beaker. The beaker is then covered and placed in a constant temperature oven maintained at 50 degrees C. After a period of about eight hours, the basic solution is decanted off and replaced with 100 ml of distilled water. The container is then returned to the oven. As noted earlier, oven temperature affects the heating time. If the temperature is reduced, the time period should be increased. After about eight to sixteen hours, the dye-containing water is siphoned or decanted off, replaced with fresh distilled water, and returned to the oven. This washing procedure is repeated until the polymer becomes yellow (indicating that all the base has been removed).

The water is then removed from the dye/gel polymer. Several methods are possible. Preferably, the polymer is washed in an anhydrous solvent having a high affinity for water, such as ethanol. This procedure is followed by centrifuging and pouring off the ethanol until the polymer takes on a powdery texture. The ethanol is then decanted off and the gel dried by evaporation.

Variations in the above treatment include: using bases other than NaOH, varying the base concentration, increasing temperature, changing the duration and frequency of the washing cycles. Also, other methods or conditions for producing hydrolysis of weak organic bonds can be used.

Figure 1:
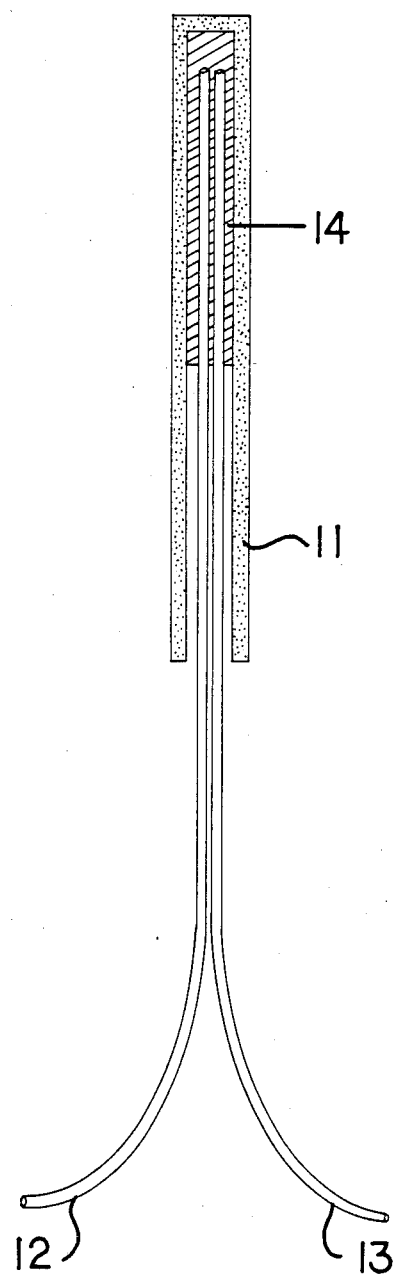
Figure 2:
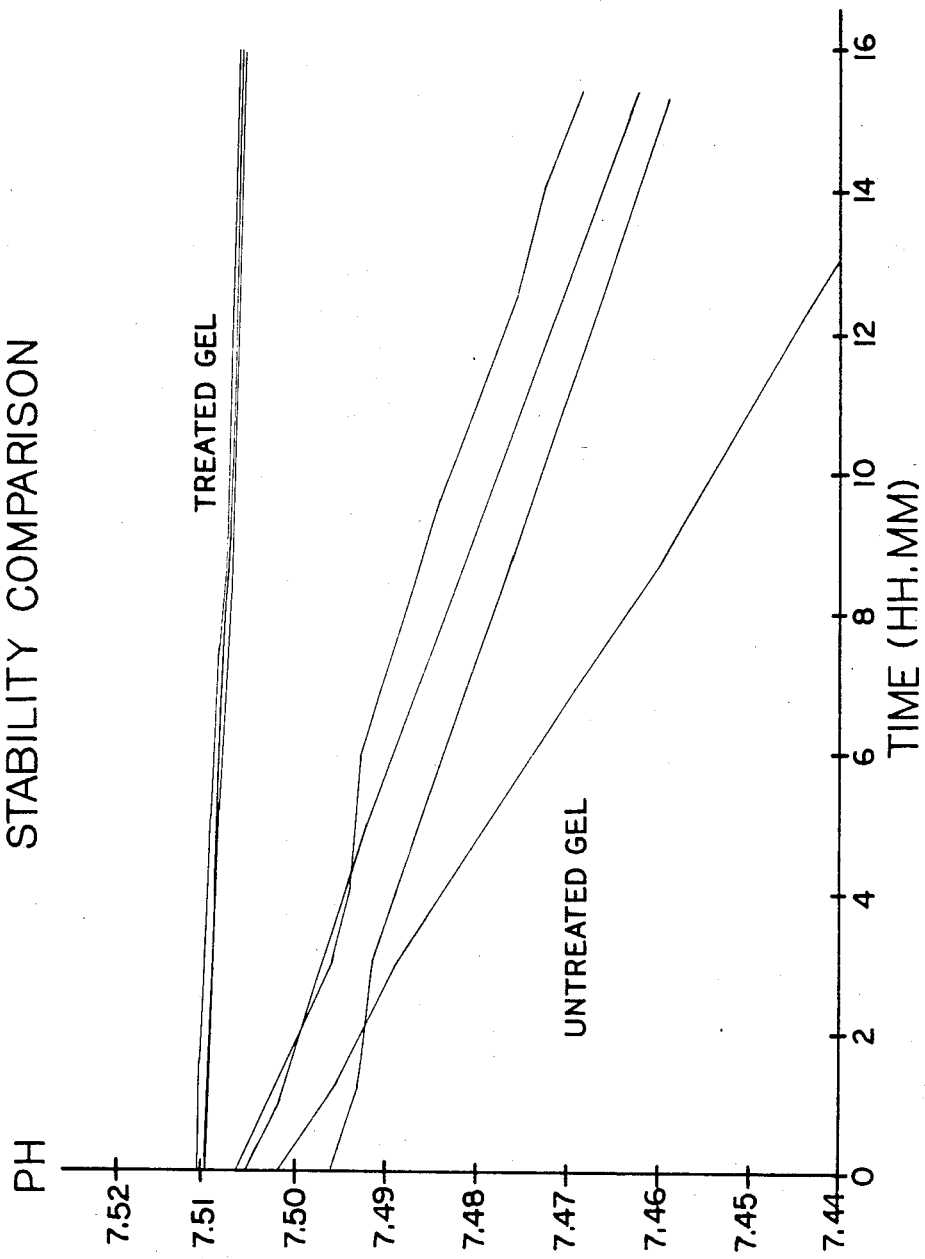

The above treatment produced pH sensors having superior drift rates. Sensors made with untreated dye/hydrogel had a drift rate of about 0.03 pH unit over ten hours and, if stored in a buffer solution for a few weeks prior to use, a drift rate of 0.015 pH unit over 10 hours could be attained. Sensors made with the treated polymer drifted less than about 0.005 pH unit in ten hours. The K values for sensors made with treated gel were also substantially more consistent than those for sensors with untreated gel, thus providing sensors that are more interchangeable and capable of being manufactured to be more nearly identical. Referring to FIG. 2, untreated gels produced a drift in pH of about 0.03 to 0.07 over 15 hours whereas treated gels produced a drift in pH of less than about 0.005 over 16 hours.

A comparison of the pH's for slurries made from several batches of polymer is shown in Table I.

TABLE I

| Batch | pH (Before Treatment) | pH (After Treatment) |
|---|---|---|
| A | 6.2 | 4.7 |
| B | 6.2 | 4.6 |
| C | 7.0 | 4.6 |
| D | 7.0 | 4.7 |
| E | 5.2 | 4.6 |

Thus, the foregoing treatment produces a dye/gel polymer which is chemically and optically stable with respect to dye loss with time, and can be used to produce nearly drift-free pH sensors and pH-based sensors (such as sensors for $CO_2$, $SO_3$ and so on). Such polymers have consistently repeatable K values and are characterized by optical stability with respect to absorbance changes with time.

Although the invention has been described and illustrated in detail, it is to be clearly understood that the same is by way of illustration and example only, and is not to be taken by way of limitation; the spirit and scope of this invention being limited only by the terms of the appended claims.

What is claimed is:

1. A method of treating a chemically and optically unstable hydrophilic acrylic dye/gel polymer which when used as a pH sensor exhibits a drift rate of about 0.03 pH unit or more over a 10 to 15 hour period to convert said unstable polymer to one having its chemical and optical stability with respect to dye loss with time increased to a point at which said polymer exhibits substantially reduced pH drift when used as a pH sensor, said method comprising:
    (1) treating said unstable polymer with an aqueous solution of a base,
    (2) washing the base-treated polymer with water to remove substantially all the base, and
    (3) contacting the washing polymer with an anhydrous solvent having a high affinity for water to remove water from said polymer.

2. A method as recited in claim 1 in which said unstable hydrophilic acrylic dye/gel polymer's pH drift over a 16 hour period is reduced by at least about one order of magnitude.

3. A method as recited in claim 1 in which said unstable hydrophilic acrylic dye/gel polymer's pH drift over a 16 hour period is reduced to less than about 0.005 pH unit.

4. A method as recited in claim 3 in which said unstable hydrophilic acrylic dye/gel polymer comprises a polyacrylamide polymer.

5. A method as recited in claim 4 in which said dye is phenol red.

6. A method as recited in any one of claims 1-5, inclusive, in which said base is sodium hydroxide.

7. A method as recited in claim 6 in which said anhydrous solvent is anhydrous ethanol.

8. A method of treating a chemically and optically unstable polyacrylamide/phenol red dye/gel polymer which when used as a pH sensor exhibits a drift rate of about 0.03 pH unit or more over a 10 to 15 hour period to convert said unstable polymer to one having its chemical and optical stability with respect to dye loss with time increased to a point at which said polymer exhibits a pH drift over a 16 hour period of less than about 0.005 pH unit when used as a pH sensor, said method comprising:
    (1) treating said unstable polymer with an aqueous sodium hydroxide solution,
    (2) washing the thus-treated polymer with water to remove substantially all the sodium hydroxide, and
    (3) contacting the washed polymer with anhydrous ethanol to remove water from said polymer.

9. A chemically and optically stable hydrophilic acrylic dye/gel polymer produced by the method of claim 1.

10. A chemically and optically stable hydrophilic polyacrylamide/phenol red dye/gel polymer produced by the method of claim 8.

* * * * *